United States Patent [19]

Skubitz et al.

[11] 4,245,642
[45] Jan. 20, 1981

[54] LEAD CONNECTOR

[75] Inventors: Frank Skubitz, Crystal; Roger L. Funk, Cedar, both of Minn.

[73] Assignee: Medtronic, Inc., Minneapolis, Minn.

[21] Appl. No.: 53,000

[22] Filed: Jun. 28, 1979

[51] Int. Cl.³ .............................................. A61N 1/00
[52] U.S. Cl. .................................................. 128/419 P
[58] Field of Search ....................... 128/419 P, 419 PS

[56] References Cited

U.S. PATENT DOCUMENTS

| | | | |
|---|---|---|---|
| 3,683,932 | 8/1972 | Cole | 128/419 P |
| 3,871,382 | 3/1975 | Mann | 128/419 P |
| 4,105,037 | 8/1978 | Richter et al. | 128/419 P |

FOREIGN PATENT DOCUMENTS 2802060 11/1978 Fed. Rep. of Germany ....... 128/419 P

*Primary Examiner*—William E. Kamm
*Attorney, Agent, or Firm*—John L. Rooney; Lew Schwartz; Joseph F. Breimayer

[57] ABSTRACT

Lead connector for use between an external pulse generator and a pacing lead. The lead connector includes elongated geometrical spaced connector pins which plug into connector terminals of the pulse generator and a hole accepting the connector end of the pacing lead. A case of the lead connector supports a pressure plate which is spring biased against a thumbscrew and engages a connector of the pacing lead against the connector pins of the lead connector.

7 Claims, 7 Drawing Figures

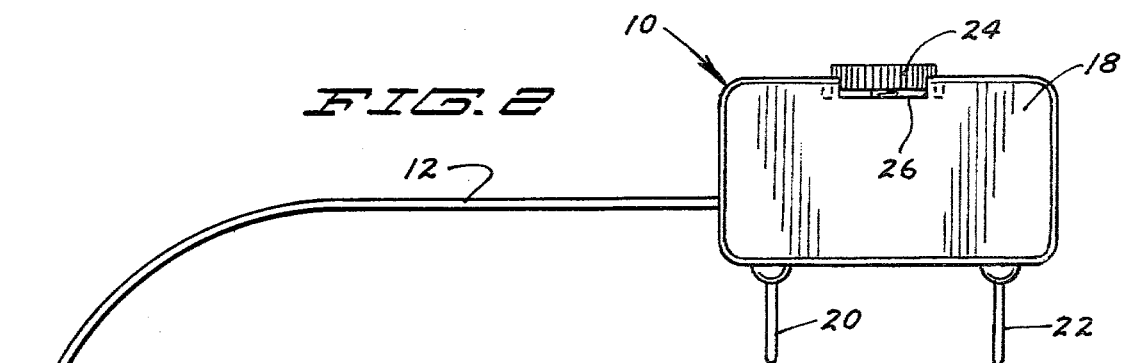
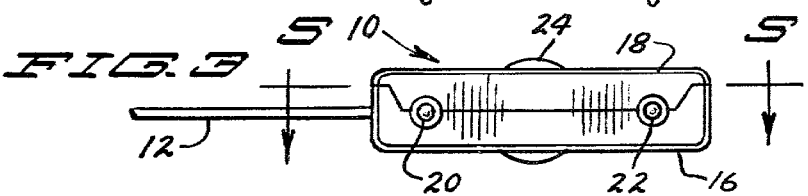
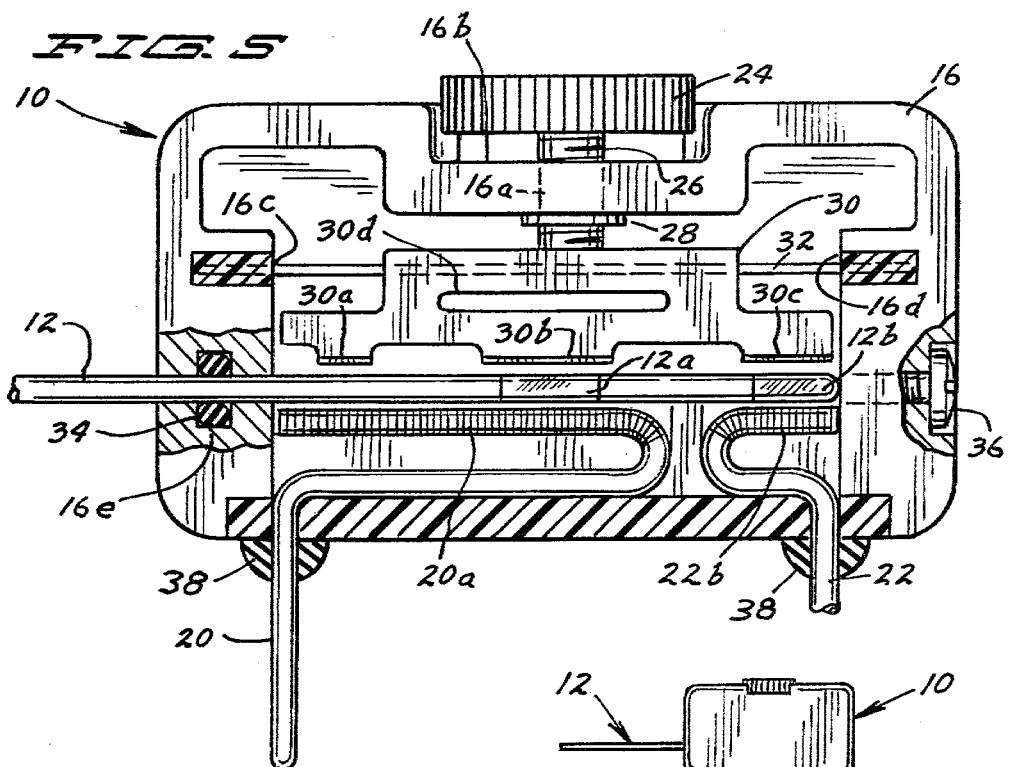
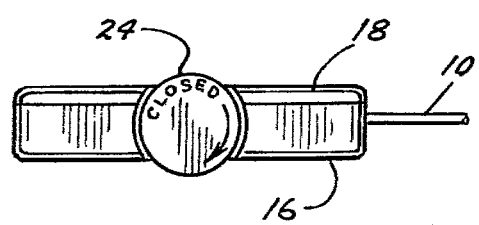
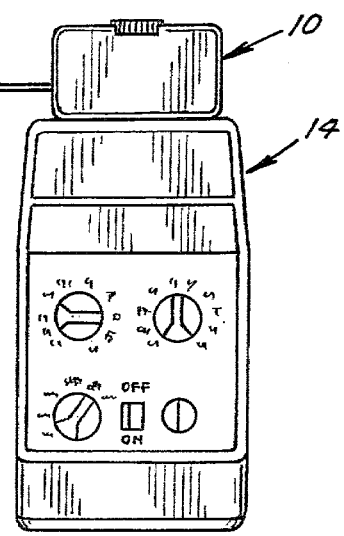

LEAD CONNECTOR

BACKGROUND OF THE INVENTION

1. Field of the Invention

The present invention relates generally to surgical electrical applicators, and more particularly, pertains to a lead connector between a pacing lead and a pulse generator.

2. Background of the Invention

There has always been a need for a connector to easily and quickly connect a temporary pacing lead to a pulse generator. The present invention fulfills this need.

Pulse generators have usually utilized binding posts for temporary connection or squeeze connectors for temporary connection which has required a certain amount of dexterity for the temporary lead or leads to be attached. Bottom connectors have been supplied in the past to connect the leads to the pulse generator.

With the advent of new temporary pacing leads, a need has existed in the art for a connector to connect the temporary pacing lead such as a TEMPTRON ® temporary lead size 4 and 5 F manufactured by Medtronic, the assignee of the present invention, to an external pacemaker such as a Medtronic ® external pacemaker Models 5375 and 5880A. This need has existed with the advent of the temporary leads and with the advent of the temporary pacemaker to connect the two together without utilizing complex inner-connecting cables or inner-connecting structure.

The present invention overcomes the disadvantages of the prior art problems in providing a lead connector.

SUMMARY OF THE INVENTION

The general purpose of this invention is to provide a lead connector between a temporary pacing lead and an external pulse generator which is easily utilized by medical personnel.

According to a preferred embodiment of the present invention, there is provided a lead connector for use between a transvenous pacing lead and an external pulse generator. The lead connector has a case back having a configured geometrical interior, a corresponding see-through case front, a positive U-shaped elongated connector pin, and a negative U-shaped elongated connector pin smaller in size than said positive connector pin. Both of the connector pins are supported and anchored in the lower portion of the case back. The connector also has a knob including a threaded screw extending down through the top of the case back including a clip on the threaded screw preventing the knob from being screwed out of the top of the case back, a pressure plate in corresponding geometrical arrangement to the case back which engages against the connector pins when forced down against the connector pins, a wire spring extending between the sides of the case back and through the plate biasing the plate into a predetermined non-engagement position, an O-ring on one side of the case back providing for a secure enclosure of the pacing lead in the case back, and a screw on the opposing side of the case back providing for cleanout. The transvenous pacing lead is inserted through the hole in the side of said case back into abutting engagement with the other side of the case back against the screw. The thumb knob forces the pressure plate to engage the transvenous pacing lead against the connector pins in a predetermined engaged position.

The pressure plate is configured to accept transvenous pacing leads having different electrode spacings at the end of the pacing lead. The geometric structure of the pressure plate is later described in detail with respect to contact spacing of the positive connector pin and the negative connector pin.

A significant aspect and feature of the present invention is that the lead connector is semi-permanent meaning that the lead connector can be used with an external pulse generator such as a demand pacemaker for any period of time. The lead connector provides for secure physical, electrical connection between the pacing lead and the external pacemaker. The lead connector can be semipermanently installed in the external pacemaker until the individual either no longer uses a pulse generator or in the alternative, until a pulse generator is implanted in the individual's body.

Another significant aspect and feature of the present invention is a see-through case front so that medical personnel such as the cardiologist can see that the pacing lead is properly inserted and physically secured within the lead connector. The lead connector being see-through provides visual feedback to the user.

The lead connector of the present invention is cleanable by removing the set screw on the side of the back case, and more importantly, sterilizable. The lead connector can be sterilized either in an autoclave, or in the alternative, in a gaseous atmosphere.

The lead connector of the present invention is simplistic in design which negates any cause of failure or misuse. The lead connector is practical and reuseable which provides a cost saving over the prior art disposable type of lead connectors.

The lead connector of the present invention saves time and provides an easy degree of operability for the medical personnel utilizing the lead connector, whether the lead connector is used in the operating room or in adjacent medical facilities.

The lead connector of the present invention is constructed from readily available materials for cost saving and is plastic injection molded from polysulfone or other like materials. The lead connector is an off-the-shelf device of readily available components meeting a need which has existed in the medical field.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the FIGURE thereof and wherein:

FIG. 1 illustrates a plan view of a lead connector between a pacinag lead and a pulse generator;

FIG. 2 illustrates an enlarged view of the lead connector with the pacing lead inserted therein;

FIG. 3 illustrates a bottom view of the lead connector;

FIG. 4 illustrates a top view of the lead connector;

FIG. 5 illustrates an enlarged exploded view of the lead connector with the front case removed and prior to engagement of a pressure plate against the pacing lead;

DESCRIPTION OF THE PREFERRED EMBODIMENT

Figure 6:
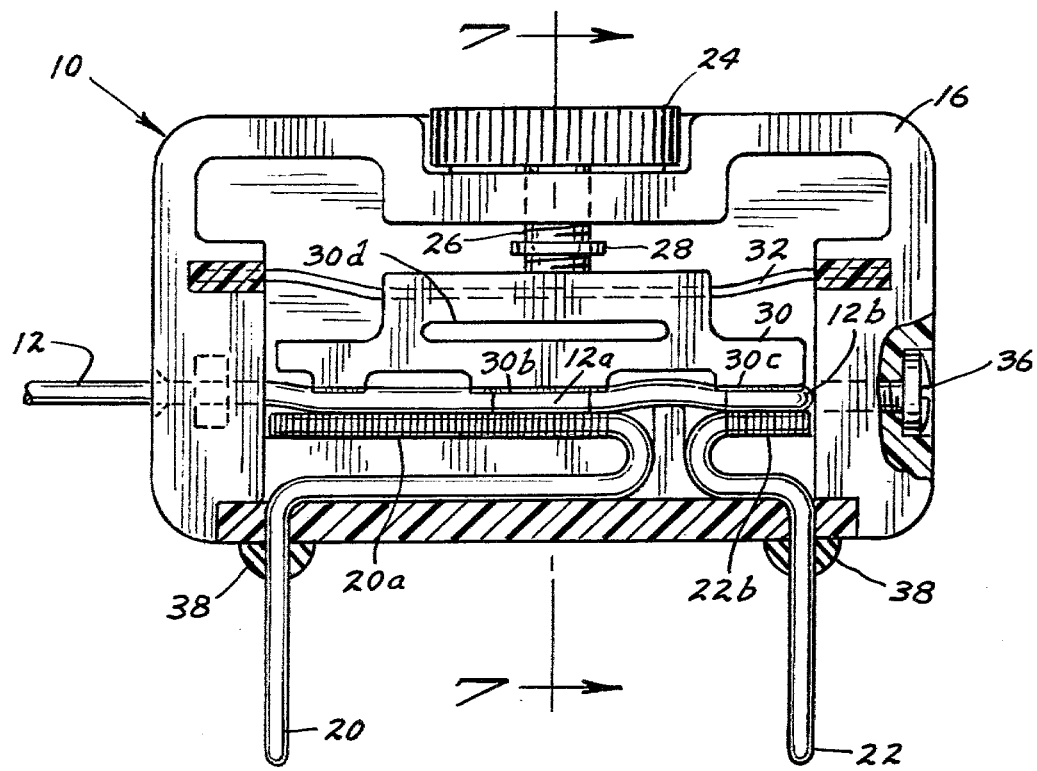
FIG. 6 illustrates the enlarged view of the lead connector with the pacing lead engaged between the pressure plate and connector pins.

FIG. 1 illustrates a plan view of a lead connector 10 between a transvenous pacing lead 12 and an external pulse generator 14. The lead 12 can be any cardiac pacing lead having appropriate external metal connectors as later described in detail. The external pulse generator 14 can be any external demand pulse generator or the like intended for use with a cardiac pacing system for temporary demand or asychronous pacing including connector terminals which align with terminals of the pacing lead 12 as later described.

FIG. 2 illustrates a front plan view of the lead connector 10 with the pacing lead 12 in electrical communication with the lead connector 10. Lead connector 10 includes a back case 16 as illustrated in FIG. 3, a front case 18 illustrated in the figures, a positive pin connector 20, a negative pin connector 22 as later described in detail, and a knob 24 including a threaded screw 26.

FIG. 3 illustrates a bottom view of the present invention where all numerals correspond to those elements previously delineated.

FIG. 4 illustrates a top view of the present invention where all numerals correspond to those elements previously delineated.

FIG. 5, which illustrates a cross-sectional view of the present invention taken along line 5—5 of FIG. 3, shows the lead connector 10 including the back case 16, the positive pin connector 20 which is a geometrical elongated U-shaped member with a hooked pin, negative connector 22 which is a geometrical elongated U-shaped connector with a hooked pin, and a knob 24 including a threaded shaft 26 which screws in through a threaded portion 16a of the back case 16. The top 16b of the back case 16 is indented providing for substantially flush engagement of the knob 24 into the indentation of the top of the back case 16. A clip 28 mechanically engages onto a lower portion of the threaded screw 26 between a wire spring 32 later described in detail and the interior of the back case 16 preventing removal of the knob 24 and the attached threaded screw 26. A pressure plate 30 including the wire spring 32 extending therethrough is accepted within the geometrical rectangular interior of the back case 16 and the ends of the wire spring 32 are accepted within indentations of 16c and 16d in the sides of the back case 16. The pressure plate 30 includes a plurality of distinct pressure points, delineated as 30a, 30b, and 30c by way of example and for purposes of illustration only spaced along a longitudinal member. The pressure points 30a and 30b coincide with the upper portion of the positive pin connector 20 while the pressure point 30c coincides with the upper portion of the negative pin connector 22. The pressure points 30a, 30b and 30c are provided with opposing outwardly extending members to encompass the metal connectors of lead 12 where members 30b.1 and 30b.2 are illustrated in the cross-sectional view of FIG. 7. The longitudinal hole 30d provides for even pressure throughout the longitudinal length of the pressure plate along points 30a through 30c. An O-ring groove 16e is provided in the back case 16 and supports an O-ring 34 having an inner diameter equal to the outer diameter of the pacing lead 12. A screw 36 is threaded into the opposing threaded side of the case back 16 and is counterbored so that the head of the screw 36 is flush with the side of the back case 16. The final component of the lead connector 10 is the see-through front case 18 which is a clear member of plastic material such as polysulfone or the like which is subsequently suitably secured to the case back 16. Grommets 38 over pins 20 and 22 provide case integrity.

PREFERRED MODE OF OPERATION

The lead connector 10 of FIG. 5 is illustrated in a ready-to-use position where the thumb screw 24 is counterclockwise in a nonengageable position, the pressure plate 30 is spaced from the connector pins 20 and 22, and the spring 32 is not in a tension condition. Subsequently and prior to use, the lead connector 10 is sterilized in either an autoclave or gaseous environment. Screw 36 can be removed to facilitate cleaning and sterilizing of the inside of the lead connector 10. Appropriately, and if required, a pipe cleaner or other like cleaning device can be run through the hole between the O-ring 34 and the screw hole 36.

In use, the pacing lead 12 is inserted into the sterilized lead connector 10 so that the tip of the pacing lead 12 abuts up against the end of the screw 36 at the side of the case back 16. Once the pacing lead 12 is inserted, the screw knob 24 is turned clockwise forcing the pressure plate 30 downwardly and subsequently forcing the pacing lead against the contact portions 20a and 22b of the connector pins 20 and 22 respectively by the spring constant of the spring 32 and the force provided by the screw 26. The turning of the thumb screw 24 continues until substantial force is required yielding a digital sensory feedback signal to the user that electrical and physical contact is established.

FIG. 6 illustrates the lead connector 10 in an engaged position with the pacing lead 12 prior to being plugged into an external pulse generator 14 as illustrated in FIG. 1. The pacing lead 12 includes the contacts 12a and 12b which are in position and in engagement against the connector pin 20a and 22b respectively as forced by the pressure plate points 30b and 30c. The spring 32 is biased downwardly as illustrated with a curvature-like bend and floats within the holes 16c and 16d respectively. The frictional engagement of the pacing lead 10 between the pressure plate 30 and the connector pins 20 and 22 prevents pulling out of the pacing lead 12 from within the lead connector 10 once the lead connector 10 is inserted and frictionally engaged in the pulse pacing generator 14.

Figure 7:
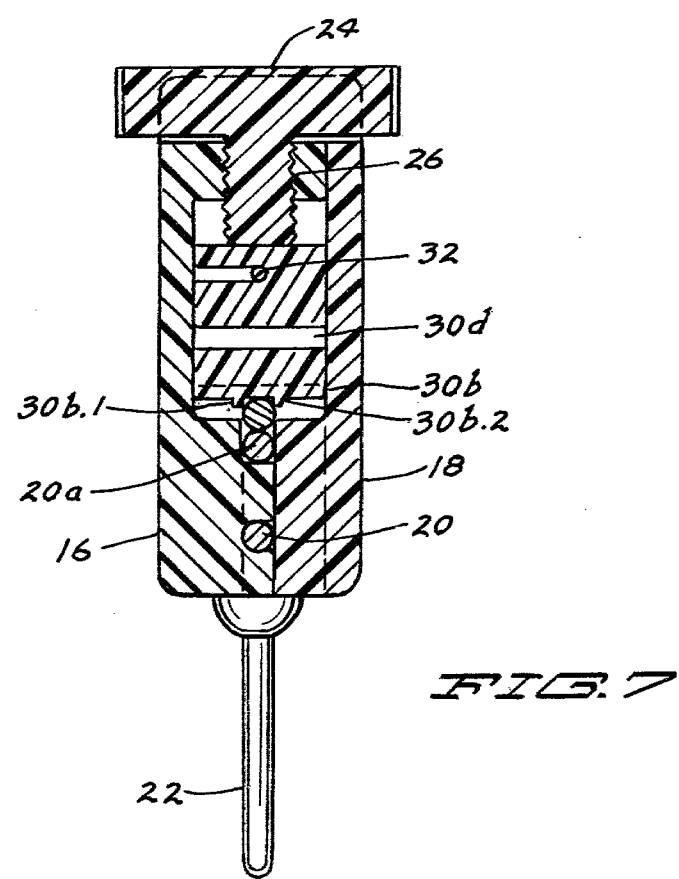
FIG. 7 illustrates a sectional view taken along line 7—7 of FIG. 6.

FIG. 7 illustrates a cross-sectional view of FIG. 6 taken along line 7—7 and shows the pacing lead 12 secured between the pressure plate 30 and the positive connector pin 20 respectively. All numerals correspond to those elements previously delineated.

Once the lead connector 10 is no longer used, the pacing lead 12 is removed by counterclockwise unscrewing of the thumb screw 24 and pulling out the pacing lead 12 through the O-ring 34. The lead connector 10 then can be reused by utilizing proper sterilization techniques. Screw 36 can also be removed for further cleaning.

Various modifications can be made to the lead connector 10 of the present invention without departing from the apparent scope thereof. For instance, in the event that the pacing lead 12 has a positive connector 12a longitudinally spaced from the end 12b a greater distance than what is presently illustrated in FIG. 5 and 7, pressure point 30a would accept the additional spacing of the positive pacing lead connector. The dimensions of the lead connector 10 are such as that the spacing of the pin connector 20 and 22 will fit into the external pulse generator and the diameter of the pacing lead is accommodated within the lead connector.

Having thus described the invention, there is claimed as new and desired to be secured by Letters Patent:

1. In combination, lead connector for use between a pacing lead having longitudinally spaced electrical connectors and an external pulse generator having spaced connector terminals comprising:
   a. enclosure means including a longitudinally extending hole whereby said pacing lead is inserted into said enclosure means and geometrically shaped connector pin means supported within said enclosure means and aligned with said longitudinal hole whereby said lead connector is plugged into said external pulse generator engaging said connector pin means in said spaced connector terminals;
   b. spring biased pressure plate means retained in slideable engagement within said enclosure means, and;
   c. adjustable means urging said pressure means against said connector pin means whereby said adjustable means urges said spring biased pressure plate means against said connector pin means encompassing said electrode means therebetween thereby providing electrical communication between said connector terminals of said pulse generator to said longitudinally spaced electrical connectors of said pacing lead through said connector pin means of said lead connector.

2. The combination of claim 1 wherein said enclosure means includes a back case and a corresponding front case, means supporting said spring biased pressure plate means in said back case, and means supporting said connector pin means in said back case, said connector pin means including a positive and a negative geometrical elongated pin protruding downward through said back case.

3. The combination of claim 1 wherein said pressure plate means includes a longitudinal member having a plurality of distinct spaced pressure points whereby each of said longitudinally spaced electrical connectors of said pacing lead is engaged by a different one of said plurality of distinct spaced pressure points.

4. The combination of claim 1 wherein said adjustable means comprises a thumbscrew.

5. The combination of claim 1 or claim 2 or claim 3 or claim 4 wherein a portion of said enclosure means is transparent thereby enabling visual inspection of said pacing lead after insertion into said enclosure means.

6. A connector for electrically coupling a pacing lead having an electrical connection to a pulse generator wherein said pulse generator has a connector terminal, comprising:
   an enclosure having a hole for insertion of said pacing lead to enclose said electrical connection;
   a connector pin mechanically affixed to said enclosure enabling electrical contact with said electrical connection of said pacing lead for insertion into said connector terminal of said pulse generator;
   a pressure plate sideably mounted in said enclosure; and
   an adjustment means attached to said enclosure for causing said pressure plate to frictionally hold said electrical connection of said pacing lead in contact with said connector pin.

7. A connector according to claim 6 wherein a portion of said enclosure is transparent enabling visual inspection of said pacing lead.

* * * * *

UNITED STATES PATENT AND TRADEMARK OFFICE
CERTIFICATE OF CORRECTION

PATENT NO. : 4,245,642
DATED : January 20, 1981
INVENTOR(S) : Frank Skubitz, Roger L. Funk It is certified that error appears in the above-identified patent and that said Letters Patent are hereby corrected as shown below:

Column 1, line 49, insert --lead-- between "The" and "connector".
Column 1, line 62, delete "The" (second occurrence in line) and insert --A-- therefor.
Column 2, line 55, "pacinag" should be --pacing--

Signed and Sealed this

Fourteenth Day of April 1981

[SEAL]

Attest:

RENE D. TEGTMEYER

Attesting Officer     Acting Commissioner of Patents and Trademarks